United States Patent [19]
Bontoux et al.

[11] Patent Number: 5,797,966
[45] Date of Patent: Aug. 25, 1998

[54] PAINLESS ELECTRIC STIMULATION APPLIANCE AND CORRESPONDING PROCESS

[75] Inventors: Daniel Bontoux, Saint-Genis-Laval; Monique Paget; Jean-Pierre Debourg, both of Lyons, all of France

[73] Assignee: Seb S.A., Ecully, France

[21] Appl. No.: 819,336

[22] Filed: Mar. 18, 1997

[30] Foreign Application Priority Data

Mar. 20, 1996 [FR] France ................................ 96 03462

[51] Int. Cl.$^6$ ........................................................ A61N 1/26
[52] U.S. Cl. ................................................................ 607/3
[58] Field of Search ........................................ 607/3, 1, 2

[56] References Cited

U.S. PATENT DOCUMENTS 4,010,742 3/1977 Kim.

FOREIGN PATENT DOCUMENTS

| 0 544 544 | 6/1993 | European Pat. Off. . |
| 2 563 437 | 10/1985 | France . |
| 2 706 131 | 12/1994 | France . |
| WO 95/04516 | 2/1995 | WIPO . |

Primary Examiner—Scott M. Getzow
Attorney, Agent, or Firm—Young & Thompson

[57] ABSTRACT

A painless electric stimulation appliance for body care comprises at least one stimulation electrode (24, 25) and a vibrating part (23) positioned in the vicinity of the electrode, which mechanically prompts the skin in vibration in association with the electric stimulation. The vibrating part is mechanically actuated by the rotation around an axis (18) of a rotating element (22) which is in turn driven mechanically in rotation.

12 Claims, 2 Drawing Sheets

PAINLESS ELECTRIC STIMULATION APPLIANCE AND CORRESPONDING PROCESS

FIELD OF THE INVENTION

This invention concerns an electric stimulation appliance for body care and a corresponding electric stimulation process. It thus relates to appliances provoking a stimulation through electric currents applied by electrodes in contact with the body, concerning body care and beauty.

BACKGROUND OF THE INVENTION

Numerous appliances making use of electric stimulation are known.

For examples, so-called anti-wrinkle appliances are known, said appliances being fitted with an electrode of small diameter which is applied on the wrinkles and is moved, a second electrode being held in the hand together with the appliance box. Harmless currents are applied and cause a well-targeted local contraction of the skin muscles. Repetition of this exercise attenuates the wrinkles. However, although the intermittently applied currents are without danger, they are perceived by many people as being unpleasant. This leads to a reduction in the intensity of the current and hence to a considerable fall in efficacy.

Face toning appliances are also known, such appliances including two electrodes between which intermittent voltages are applied. The face muscles are strengthened and thus toned up by repeated tightening and relaxing of said muscles, but the same disadvantages described above also apply in this situation.

Passive gymnastic appliances have also been proposed, such appliances including electrodes arranged on the body. Thanks to these electrodes, currents are applied to the surface of the skin, such currents exercising and tightening, for example, the stomach muscles and also helping to absorb fat.

SUMMARY OF THE INVENTION

Unfortunately, the efficiency of all these appliances involves applying electric currents to the surface of the skin, which said currents, while being without danger, are nonetheless painful and very unpleasant.

Document EP-A-0.544.544 concerns a device for relieving pain. This device includes a plurality of pain-relieving sources selected from among massage, vibration, pressure and electric stimulation, together with means for applying at least two of these sources simultaneously to a selected point of a person's upper body.

Document FR-A-2.706.131 concerns a cap which stimulates hair growth. The inside of the cap is fitted with sliding electrodes which adapt to the skull and receive adjustable electric pulses from an electronic module. The cap also includes an incorporated mechanical vibrating device.

Document U.S. Pat. No. 4,010,742 describes an electronic therapy device for treating various pains of the human body. This device possesses a vibrator including a heat source and an electrical circuit which supplies electrons to the skin of the human body by means of rollers placed in contact with the skin.

Document WO-A-95.04.516 concerns a method for massaging the face and neck with a device which applies an electric stimulation followed by a manual massage and vibratory treatment.

Document FR-A-2.563.437 describes an appliance for facilitating the impregnation and penetration of, in particular, the skin, using cosmetic products. The appliance has two outputs which are conformed so that each of them can be electrically connected to an adapter element. The extremity of at least one of the elements is arranged in such a way as to allow the transmission of a vibration and the conduction of a current.

This invention concerns an electric stimulation appliance for body care which eliminates or considerably reduces the painful effects of the currents applied.

The invention also concerns such an electric stimulation appliance which is both compact and easy to use.

The invention also concerns such an electric stimulation appliance which is economical to manufacture.

The invention also concerns an electric stimulation process for body care which eliminates or considerably reduces unpleasant effects.

This invention thus concerns an electric stimulation appliance for body care, comprising at least one stimulation electrode applied locally on the skin and delivering currents to it during use.

This electric stimulation appliance comprises at least one vibrating part mechanically prompting the skin in vibration in association with the electric stimulation, and a box held in the hand during use.

According to the invention, the vibrating part placed in the vicinity of the electrodes is manually actuated by rotation around an axis of at least one rotating element, this rotating element being driven mechanically in rotation.

One interpretation of this phenomenon of pain removal or reduction is that the mechanical vibrating prompt of the electric stimulation appliance saturates the neighboring nervous terminations of the electrodes by permanently maintained information serving to mask the painful effects of the electric current. Indeed, when a properly adjusted continuous vibratory prompt is superimposed on a painful, in particular intermittent prompt, the nervous influx is saturated by the vibrations and the pain is no longer felt.

It is important that the electrodes and the vibrating part or parts should cooperate with a view to producing painless electric stimulation. This is obtained when the electric stimulation appliance ensures a mechanical prompt in the vicinity of the electrodes.

The mechanical vibrations are either applied in the proximity of the electrodes, the electric stimulation appliance fulfilling a purely mechanical vibrating function, or are obtained by making the electrodes themselves vibrate, in which case the electric stimulation appliance fulfills an electromechanical vibrating function.

When in operation, the vibrating part advantageously produces a mechanical vibration at a vibration frequency approximately equal to 100 Hz.

Pain attenuation is in fact most efficient with a vibratory charge whose frequency is of this order. In any event, it is best that the vibration frequency should not exceed 300 Hz, as the nervous response is no longer proportional to the prompt frequency beyond this point.

When in operation, the vibrating part preferably produces a mechanical vibration with an amplitude lying between $1/5$ mm and 1 mm.

In an advantageous form of embodiment, the electric stimulation appliance comprises a metal part external to the box, and by which said box is held in the hand, this metal part acting as ground electrode.

3

In a first preferred embodiment, the vibrating part is dissociated from the electrodes.

In a second preferred embodiment of the electric stimulation appliance according to the invention, the vibrating part carries at least one of the stimulation electrodes.

According to a first advantageous form of this second embodiment, the stimulation electrodes being two approximately parallel electrodes applied simultaneously in operation on a surface of the skin, the appliance comprises:

a box, a support carrying the two stimulation electrodes, elastic means flexibly linking the support to the box, a flyweight positioned on the support along a rotation axis crossing it, the flyweight being off-center in relation to the axis, and means for driving the flyweight in rotation, in such a way that a rotating drive of the flyweight causes a movement of the support holding the stimulation electrodes which is approximately perpendicular to the surface of the skin.

In a second advantageous form of this second embodiment, the electric stimulation appliance comprises:

a box, two rollers having approximately parallel axes around which they are mobile, the rollers being linked to the box and connected to a source of voltage in such a way as to constitute the stimulation electrodes applied to the skin when in operation, driving means of at least one of the rollers in vibratory rotation, mechanically prompting the skin in vibration.

In this second advantageous form of embodiment, it is also useful for the stimulation appliance to comprise means of driving the roller in continuous rotation, the effects of said means of continuous rotation being superimposed on those of vibratory rotation.

Moreover, a first roller being driven by driving means, it is advantageous that that the second roller should be braked in rotation so as to facilitate the formation of a fold on the skin when the appliance is being applied.

The invention also concerns an electric stimulation process for body care which is both esthetic and fortifying.

According to the invention, the electric stimulation and a vibratory mechanical prompt produced by the mechanical actuating of at least one vibrating part are applied simultaneously and in a same local area of the skin, through rotation around an axis of at least one rotating element driven mechanically in rotation.

BRIEF DESCRIPTION OF THE DRAWINGS

Other particularities and advantages of the appliance and process according to the invention will emerge from the ensuing description given for purely illustrative purposes, with reference to the accompanying drawings in which.

DESCRIPTION OF THE PREFERRED EMBODIMENTS

Figure 1:
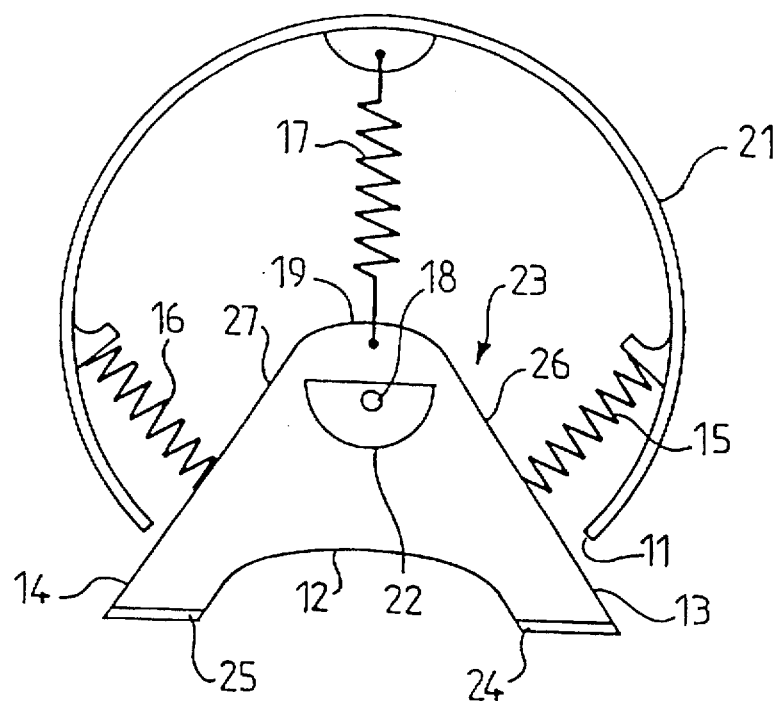
FIG. 1 gives a cross-section view of a first embodiment of the electric stimulation appliance according to the invention.

In a first embodiment of the electric stimulation appliance according to the invention, as represented in FIG. 1, the appliance comprises two stimulation electrodes 24 and 25 applied on the skin and producing vibrations by themselves.

4

The electric stimulation appliance in this first embodiment comprises a body 21 or box, approximately circular cylindrical in form, and a vibrating part 23. The latter has a solid form of approximately triangular cross-section. The cross-section of the vibrating part 23 includes a base 12, a top 19 and lateral walls 26 and 27 linking the base 12 to the top 19. Lugs 13 and 14 project laterally from the base 12 in the prolongation of the lateral walls 26 and 27. The stimulation electrodes 24 and 25 are placed respectively at their extremities. The stimulation electrodes 24 and 25 are thus wide and set apart.

For example, the width of the stimulation electrodes 24 and 25 is equal to 8 mm and their distance apart is 20 to 30 mm.

Most of the vibrating part 23 is placed in the body 21, the top 19 being orientated towards the interior of the body 21, and the base 12 exiting from the body 21 by an opening 11.

The vibrating part 23 is attached to the body 21 by elastic means providing a flexible connection. These means consist, for example, of springs 15, 16 and 17 respectively linked to the lateral walls 26 and 27 and to the top 19.

In addition, the vibrating part 23 carries a shaft 18 positioned about a third of the way between the top 19 and the base 12. This shaft 18 is flexibly mobile inside the body 21, being for example attached to a fixed shaft by an elastic joint. The shaft 18 is integral with an off-center flyweight 22, having an approximately half-disk form, disposed on the vibrating part 23. The body 21 of the appliance contains an electric motor driving, when in operation, the shaft in rotation, and thus causing an approximately translatory movement of the vibrating pail 23 through the opening 11.

When in use, the stimulation electrodes 24 and 25 are electrically supplied, for example by internal electronics, and the electric motor turns the flyweight 22 which moves the vibrating pail 23. The moving stimulation electrodes 24 and 25 are periodically applied on the skin and thus communicate vibrations to the skin prior to electric pulses. The width and separation of the electric pulses emitted are such as to cause a sufficiently large area of the skin, situated between and around the electrodes, to be contracted by pulses. As a result, they possess an action which increases muscle development and thus has a tonic effect. The vibrations of the vibrating part 23 are such that the electric pulses are felt little if at all.

The shaft 18 is advantageously rotated at a frequency of the order of 100 Hz.

Figure 2:
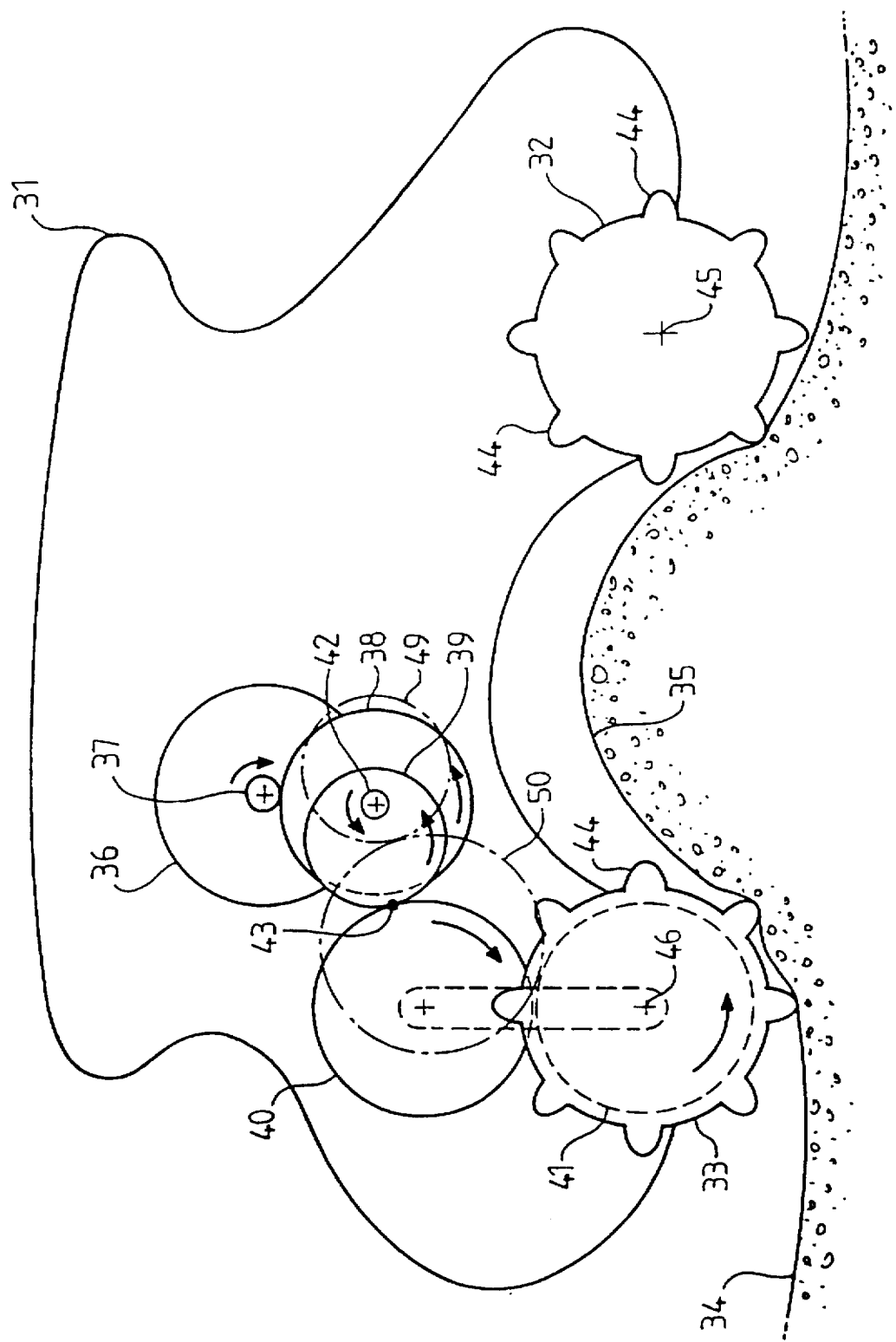
FIG. 2 schematizes in a longitudinal cut a second embodiment of the electric stimulation appliance according to the invention.

In a second embodiment, illustrated in diagram form in FIG. 2, the electric stimulation appliance comprises a body 31 or box which may be held in the hand, and two rollers 32 and 33 partially contained in the body 31. The rollers 32 and 33 have parallel axes, respectively 45 and 46, and are equipped with teeth 44. As an example, each of the rollers 32, 33 includes eight teeth 44. A first roller 32 is braked, while the second roller 33 is rotated by driving means. The rollers 32 and 33 are electrical conductors and connected to a voltage source so as to constitute the stimulation electrodes applied on the skin. For example, they are covered with a deposit of silver or are made up of a conductive plastic.

The rotating drive means of the second roller 33 comprise a motor 36 acting on the roller 33 by a kinematic chain. This kinematic chain causes a rotating movement comprising both a continuous component and an alternating component, the latter having a vibratory frequency. In the embodiment example, the kinematic chain includes a first wheel 37 geared to a second wheel 38 which is fixed and usually centered on a shaft 42. A third wheel 39 is fixed on the same shaft 42, but off-center. The third wheel 39 is geared to a fourth wheel 40 which is in turn geared to a fifth wheel 41 integral with the second roller 33. The fourth wheel 40 oscillates around the fifth wheel 41 so as to maintain the gearing with the third wheel 39.

When in use, the rollers 32 and 33 are applied simultaneously on the skin 34. The motor 36 is activated and drives the second roller 33 in rotation, while the first roller 32 is braked. In this way a fold of skin 35 is formed between the rollers 32 and 33, this said fold 35 progressing as the appliance is moved. The appliance thus serves as a vibrator with parallel rollers performing a "palpating-rolling" action on the skin 34. Simultaneously, an intermittent voltage of known type is applied between the rollers 32 and 33, and the currents generated in the fold 35 increase the efficacy of the massage. The contraction of the muscles of the fold 35 absorbs fat far more efficiently than is the case when there is no electric stimulation.

Owing to the kinematic chain, a regular and continuous drive of the motor 36 causes the superimposition of continuous and alternating rotation movements of the second roller 33. Thus, in the position indicated by the line of continuous dashes in FIG. 2, the gearing point 43 of the wheels 39 and 40 is far removed from the shaft 42, with the result that the fourth wheel 40 and the second roller 33 revolve quickly. In contrast, in a second position of the wheels 39 and 40, illustrated respectively by the dot-and-dash line at the positions 49 and 50, the gearing point 43 is close to the shaft 42, and the wheel 40 and the second roller 33 turn gently. These variations in the rotation speed of the second roller 33 cause the required vibrations.

The amplitude of the alternating component in relation to the continuous component is easily adjusted by varying the eccentricity of the third wheel 39 which acts as driving wheel. If the shaft 42 is outside the pitch circle of the third wheel 39, a periodic counter-movement may even be obtained.

The vibratory prompts obtained by the appliance render the electric stimulation obtained both efficient and painless.

Preferably, the alternating rotation movement has a frequency of the order of 100 Hz.

The references inserted after the technical characteristics mentioned in the claims are provided solely for the purpose of facilitating comprehension of said characteristics and in no way limit their scope.

We claim:

1. Electric stimulation appliance for body care, comprising at least one stimulation electrode (24, 25, 32, 33) applied locally on the skin and sending skin currents when in operation, at least one vibrating part (23, 33) mechanically prompting the skin in vibration in association with a electric stimulation, and a box (21, 31) held in the hand during use, characterized in that said vibrating pair (23, 33) being positioned in the vicinity of said electrodes (24, 25, 32, 33) is mechanically actuated by the rotation around an axis (18, 46) of at least one rotating element (22, 23), said rotating element being driven mechanically in rotation.

2. Electric stimulation appliance according to claim 1, characterized in that said vibrating part (23, 33) produces, when in operation, a mechanical vibration at a vibration frequency approximately equal to 100 Hz.

3. Electric stimulation appliance according to claim 1, characterized in that said vibrating part (23, 33) produces, when in operation, a mechanical vibration with an amplitude lying between ⅕ mm and 1 mm.

4. Electric stimulation appliance according to claim 1, characterized in that it comprises a metal part external to the box, and by which said box is held in the hand, this metal part acting as ground electrode.

5. Electric stimulation appliance according to claim 1, characterized in that the vibrating part is dissociated from said electrodes.

6. Electric stimulation appliance according to claim 1, characterized in that said vibrating part (23, 33) carries at least one of said stimulation electrodes (24, 25, 32, 33).

7. Electric stimulation appliance according to claim 6, characterized in that said stimulation electrodes (24, 25) being two approximately parallel electrodes applied simultaneously in operation on a surface of the skin, the appliance comprises:

a box (21), a support (23) carrying the two stimulation electrodes (24, 25), elastic means (15, 16, 17) flexibly linking the support (23) to the box (21), a flyweight (22) positioned on the support (23) along a rotation axis (18) crossing it, the flyweight (22) being off-center in relation to said axis (18), and means for driving the flyweight (22) in rotation, in such a way that a rotating drive of the flyweight (22) causes a movement of the support (23) holding the stimulation electrodes (24, 25) which is approximately perpendicular to the surface of the skin.

8. Electric stimulation appliance according to claim 6, characterized in that it comprises:

a box (31), two rollers (32, 33) having approximately parallel axes (45, 46) around which they are mobile, said rollers (32, 33) being linked to the box (31) and connected to a source of voltage in such a way as to constitute the stimulation electrodes applied to the skin when in operation, driving means (36–42) of at least one of the rollers (33) in vibratory rotation, mechanically prompting the skin in vibration.

9. Electric stimulation appliance according to claim 8, characterized in that it also comprises driving means (36–42) of said roller (33) in continuous rotation, said driving means in continuous rotation and vibratory rotation having superimposed effects.

10. Electric stimulation appliance according to claim 8, characterized in that a first roller (33) being driven by said driving means (36–42), the second roller (32) is braked in rotation so as to facilitate the formation of a fold (35) on the skin (34) during the application of the appliance.

11. Electric stimulation process for esthetic body care, characterized in that an electric stimulation and a vibratory mechanical prompt produced by the mechanical actuating of at least one vibrating part (23, 33) are applied simultaneously and in a same local area of the skin (34), by means of the rotation around an axis (18, 46) of at least one rotating element (22, 33) driven mechanically in rotation.

12. Electric stimulation process for fortifying body care, characterized in that an electric stimulation and a vibratory mechanical prompt produced by the mechanical actuating of at least one vibrating part (23, 33) are applied simultaneously and in a same local area of the skin (34), by means of the rotation around an axis (18, 46) of at least one rotating element (22, 33) driven mechanically in rotation.

* * * * *